United States Patent [19]

Dinh et al.

[11] Patent Number: 5,117,024
[45] Date of Patent: May 26, 1992

[54] PROCESS FOR PREPARATION OF PRIMARY AMINOORGANOSILANES

[75] Inventors: Paul C. Dinh; Kenneth P. Kaufman, both of Midland, Mich.

[73] Assignee: Dow Corning Corporation, Midland, Mich.

[21] Appl. No.: 740,834

[22] Filed: Aug. 6, 1991

[51] Int. Cl.⁵ .............................. C07F 7/10; C07F 7/18
[52] U.S. Cl. .................................................. 556/413
[58] Field of Search ........................................ 556/413

[56] References Cited

U.S. PATENT DOCUMENTS

| | | | |
|---|---|---|---|
| 2,449,036 | 9/1948 | Grunfeld | 260/583 |
| 3,046,295 | 7/1962 | Lisanke | 260/648.8 |
| 3,520,932 | 7/1970 | Martin | 260/589 |
| 4,186,146 | 1/1980 | Butte | 260/570.5 B |
| 4,739,120 | 4/1988 | Zuckerman | 556/385 |
| 5,001,246 | 3/1991 | Ishimura et al. | 556/413 |

OTHER PUBLICATIONS

Noll, Chemistry & Technology of Silicones, Academic Press, Inc., NY, 1968, pp. 174-176; and 180-181.

*Primary Examiner*—Paul F. Shaver
*Attorney, Agent, or Firm*—William F. Boley

[57] ABSTRACT

The present invention is a process for the preparation of primary aminoorganosilanes. The process comprises contacting an cyanoorganosilane with hydrogen gas in the presence of a supported cobalt catalyst. The result of this process is a near quantitative conversion of the cyanoorganosilane to a primary aminoorganosilane. The apparent rate and yield of the process can be improved by use of an organic solvent, without effecting specificity for the primary aminoorganosilane.

19 Claims, No Drawings

PROCESS FOR PREPARATION OF PRIMARY AMINOORGANOSILANES

BACKGROUND OF INVENTION

The present invention is a process for the preparation of primary aminoorganosilanes. The process comprises contacting an cyanoorganosilane with hydrogen gas in the presence of a supported cobalt catalyst. The result of this process is a near quantitative conversion of the cyanoorganosilane to a primary aminoorganosilane.

Primary aminoorganosilanes are useful intermediates for the preparation of aminofunctional silicone fluids, which have wide applications for fabric treatment, personal care products, and as glass coupling agents. A typical process for preparing primary aminoorganosilanes is described in Noll, Chemistry and Technology of Silicones, Academic Press, Inc., N.Y., 1968, pages 174-176. The process involves the reaction of a haloalkylsilane with an excess of ammonia, as follows:

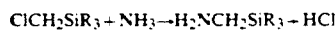

This process results in a mixture of primary and secondary amines. Typically the process is run with as much as a 20-fold excess of ammonia, to favor production of the primary amine. This process requires recovering of the ammonia for disposal or recycling and recovery and disposal of the environmental hazardous hydrogen chloride and aminohydrochloride salt by-products.

An alternative route to primary amines, that can avoid these recovery and disposal problems, is formation of cyanoorganosilanes by addition of the Si-H bond to unsaturated nitriles, as follows:

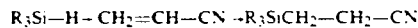

Such procedures are described in Noll, supra, pages 180-181. The nitrile group is subsequently hydrogenated to an amine.

The hydrogenation of nitrile groups is a well known process in organic chemistry. Numerous procedures are described in the patent literature, with considerable attention focused on methods of producing the primary amine without secondary amine formation.

Grunfeld, U. S. Pat. No. 2,449,036, issued Sep. 7, 1948, describes a process run in the presence of nickel or cobalt catalysts, leading to the production almost exclusively of primary amines, where the reduction is carried out in the presence of a strong base soluble in water. Grunfeld states that this process is an improvement over prior art, employing cobalt catalysts, which required the presence of ammonia to drive the reaction toward the production of primary amines.

Martin, U.S. Pat. No. 3,520,932, issued Jul. 21, 1970, describes a process for the preparation of 5-amino-2,2-dialkylpentanols by a one-step catalytic hydrogenation of 4-cyanodialkylbutyraldehydes. The process is run in the presence of a rhodium catalyst and ammonia. Rhodium is reported to be the only catalyst operative in the process.

Butte U.S. Pat. No. 4,186,146, issued Jan. 29, 1980 reports an improved process for the hydrogenation of aromatic nitriles to primary amines. The nitrile is hydrogenated in a solvent system containing added ammonia and a cobalt or nickel catalyst, with the improvement comprising employing an ether as solvent and carrying out the hydrogenation in the presence of water.

Zuckerman, U.S. Pat. No. 4,739,120, issued Apr. 19, 1988, describes an improved process for the catalytic hydrogenation of an organic nitrile group containing compound to a primary aminomethyl group in the presence of a rhodium catalyst, a basic substance, and in a two-phase solvent system comprising an immiscible organic solvent and water.

Lisanke, U.S. Pat. No. 3,046,295, issued Jul. 24, 1962, reports a process for producing primary aminoalkylsilanes. The process comprises contacting, under essentially anhydrous conditions, a cyanoalkylalkoxysilane with a diamino compound, a hydrogenation catalyst, and hydrogen under pressure. The catalyst employed is described as a Raney nickel catalyst.

Therefore, quite unexpectly, it has been found that supported cobalt catalyzes the hydrogenation of cyanoorganosilanes to primary aminoorganosilanes, with near quantative selectivity for the primary aminoorganosilane. This selectivity is achieved without the production of hydrogen chloride and without the addition of ammonia and solvents systems, as previously reported.

SUMMARY OF INVENTION

The present invention is a process for the preparation of primary aminoorganosilanes. The process comprises contacting an cyanoorganosilane with hydrogen gas in the presence of a supported cobalt catalyst. The result of this process is a near quantitative conversion of the cyanoorganosilane to a primary aminoorganosilane. The apparent rate and yield of the process can be improved by use of an organic solvent, without effecting specificity for the primary aminoorganosilane.

DESCRIPTION OF INVENTION

The present invention is a process for the hydrogenation of cyanoorganosilanes to form the corresponding primary amine. The process comprises:

(a) contacting a cyanoorganosilane of formula

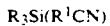

with hydrogen gas, in the presence of catalyst comprising cobalt retained on a solid support, at a temperature within a range of about 100° C. to 200° C. and a pressure within a range of about 200 psig to 2,000 psig; and (b) recovering a primary aminoorganosilane of formula

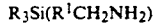

where each R is independently selected from a group consisting of alkyl and alkoxy radicals of 1 to 10 carbon atoms, aryl and aryloxy radicals of 5 to 10 carbon atoms, and hydrogen; and $R^1$ is a divalent hydrocarbon radical of 1 to 20 carbon atoms.

The present process hydrogenates cyanoorganosilanes to the corresponding primary aminoorganosilanes. Cyanoorganosilanes which can be hydrogenated by the present process are of the general formula $R_3Si(R^1CN)$. Each constituent, R, is independently selected from a group consisting of alkyl and alkoxy radicals of 1 to 10 carbon atoms. The R radical can be, for example, methyl, ethyl, propyl, isopropyl, butyl, tert-butyl, isobutyl, pentyl, dodecyl, methoxy, ethoxy, propoxy, isopropoxy, butoxy, phenyl, and phenoxy. Preferred is when R is selected from the group consisting of methyl, methoxy, ethyl, and ethoxy.

The constituent $R^1$ is a divalent hydrocarbon radical of 1 to 20 carbon atoms. The divalent radical $R^1$ can be, for example, divalent radicals of alkanes, cycloalkanes, aromatic, and aralkane compounds. The divalent radical of alkanes can be for example methylene, ethylene, propylene, ethylidene, and isopropylidene. The divalent radical of cycloalkanes can be, for example, cyclohexylene and cycloheptylene. The divalent aromatic can be for example phenylene, tolylene, xylylene, and naphthylene. The divalent radical of aralkanes can be, for example, of formula $—C_6H_4—R^2—$, where $R^2$ is methylene, ethylene, or propylene.

Examples of cyanoorganosilanes which can be hydrogenated by the instant process are: 2-cyanoethyltrimethylsilane, 2-cyanoethyldimethylmethoxysilane, 2cyanoethylmethyldimethoxysilane, 2cyanoethyltrimethoxysilane, 2-cyanoethyldimethylsilane, 2cyanoethyldimethoxysilane, 2-cyanoethyltriethoxysilane, 2cyanoethyldimethylethoxysilane, 2cyanoethylphenylmethylsilane, 2cyanoethylphenylmethoxysilane, cyanomethyltriethoxysilane, 3cyanopropyltrimethylsilane, 3-cyanopropyldimethylsilane, and 3-cyanopropylmethyldimethoxysilane.

Contacting of the cyanoorganosilane with hydrogen gas, in the presence of the catalyst, can be effected in standard high pressure reactors. The reactor can be, for example, a fixed-bed, stirred-bed, or fluidized-bed type reactor. The process can be run as a batch process or as a continuous process. A stirred-bed reactor is preferred.

Contact time for the hydrogenation process to occur is rapid and generally determined by availability of catalyst, pressure of the reactor, and reactor temperature. In general residence times of 0.2 hour to 5.0 hours are considered appropriate. When the process is run as a batch process, it is generally preferred to use residence times of 0.5 to 3.0 hours, with periodic replenishment of hydrogen as it is consumed by the reaction.

It is preferred that the process be run in the presence of a molar excess of hydrogen, where molar excess is defined as greater than two moles of hydrogen per mole of cyanoorganosilane. In general, the greater the amount of hydrogen present the faster the reaction. Therefore, in a preferred mode of operating the process, hydrogen is added in excess at a concentration sufficient to maintain the pressure within the reactor within a range of 200 psig to 2,000 psig. A more preferred pressure is within a range of about 500 psig to 1,000 psig, since these pressures allow the use of standard high pressure reactors and avoid the expense associated with the design and operation of reactors operable at higher pressures.

The catalyst comprises cobalt retained on a solid support. The method of retention of the cobalt on the solid support is not critical to the present invention. It is preferred that the cobalt not be released from the solid support during conduct of the process. The cobalt may be retained on or within the solid support by standard means, for example, adsorption, ionic bonding, covalent bonding, or physical entrapment.

The solid support material can be, for example, silica, silica gel, alumina, silica-alumina, carbon, or zeolite. The preferred solid support material is selected from the group consisting of silica, alumina, and silica-alumina. A preferred silica support is kieselguhr.

The solid support material may be in the form of, for example, flakes, chips, particles, powders, spheres, or tablets. Preferred is when the solid support material is less than about one centimeter in maximum diameter. More preferred is when the solid support material is a powder with an average particle size of about $20\mu$ to $100\mu$ in diameter. The lower size limit for the solid support material is determined by the practicalities of retaining, recovering, and handling of the material.

A useful concentration of cobalt retained on a solid support is where the cobalt comprises about 10 to 70 weight percent of the total weight of the cobalt and solid support composition. In general, the greater the amount of cobalt retained on the solid support, the more active the catalyst.

When the process is run as a batch process, it is preferred that cobalt constitute, by weight, about 0.1 to 20 percent of a reaction mixture comprising the cobalt and the cyanoorganosilane. More preferred is when cobalt constitutes about 1.0 to 10 percent, by weight, of the reaction mixture.

Although not necessary, it is preferred that the contents of the reactor be mixed during conduct of the instant method, particularly when the process is run as a batch process. Mixing can be accomplished by standard means, for example, mechanical stirring, refluxing sonification, or turbulence created by addition of reactants to the reactor.

The present process can be conducted at a temperature within a range of 50° C. to 250° C. A preferred temperature range is 100° C. to 200° C. The most preferred temperature for conducting the process is within the range of 150° C. to 175° C.

It is preferred that the process be conducted in the presence of an organic solvent. The use of an organic solvent increases the apparent rate and yield of the process, but appears to have no effect on selectivity. The organic solvent can be a polar or non-polar solvent. Preferred is a polar organic solvent. The polar solvent can be an alcohol, for example, methanol, ethanol, propanol, or isopropanol. The organic solvent can be a non-polar solvent, for example, benzene, toluene, or xylene. When the process is conducted as a batch process, it is preferred that the solvent be present as about 5 to 50 weight percent of the reaction mixture, where the reaction mixture comprises the solvent, cobalt, and cyanoorganosilane. More preferred, is when the solvent is present as about 10 to 20 weight percent of the reaction mixture.

When the process is conducted as a continuous process, the cyanoorganosilane feed can be diluted in the organic solvent, where the cyanoorganosilane comprises about 50 to 95 percent of the liquid feed to the reactor. Preferred is when the cyanoorganosilane comprises about 80 to 90 weight percent of the liquid feed to the reactor.

Product primary aminoorganosilanes are recovered from the process. The primary aminoorganosilanes can be recovered by standard means for separating liquid-solid mixtures and mixtures of liquids, for example, filtration and/or distillation.

Primary aminoorganosilanes that can be produced by the present process are, for example, 3aminopropyltrimethylsilane, 3-aminopropyldimethylmethoxysilane, 3aminopropylmethyldimethoxysilane. 3aminopropyltrimethoxysilane, 3-aminopropyldimethoxysilane, 3aminopropyldimethoxysilane, 3-aminopropyltriethoxysilane, 3aminopropyldimethylethoxysilane, 3 aminopropylphenylmethylsilane, 3aminopropylphenylmethoxysilane, 2-aminoethyltriethoxysilane, 4-aminobutyltrimethylsilane, 4-aminobutyldimethylsilane, and 4-aminobutylmethyldimethoxysilane.

In order that those skilled in the art may better understand how the present invention may be practiced, the following examples are given. These examples are given for illustration only and are not meant to be limiting on the present claims.

EXAMPLE 1

The hydrogenation of 2-cyanoethylmethyldimethoxysilane in the presence of a cobalt supported on kieselguhr catalyst was evaluated. The reactor was a one-liter Parr reactor equipped with an air-driven agitator a cooling coil, and a thermocouple. To the reactor was added 30.0 g of 2-cyanoethylmethyldimethoxysilane, 81.1 g of methanol as solvent and 4.5 g of cobalt on kieselguhr. The cobalt on kieselguhr catalyst was purchased from United Catalyst, Inc. (Louisville Ky., Cat. No. G-61). The catalyst was in the form of a powder containing about 67 percent, by weight, cobalt.

The Parr reactor was sealed, then pressurized and vented alternately five times with hydrogen at 200 psig. On the sixth cycle, the hydrogen pressure within the reactor was adjusted to 250 psig, the reactor was leak tested for 15 min., and then the agitator and heater were turned on. After the temperature stabilized at 150° C., the reactor was pressurized with hydrogen to 750 psig and maintained at about 750 psig during the remainder of the process by intermittently repressurizing the reactor with hydrogen as the hydrogen was consumed. After two hours of reaction, hydrogen uptake ceased. The reactor was cooled to room temperature, excess pressure vented, and the crude reaction mixture recovered. The mixture was filtered to remove the catalyst. The clear liquid supernate was collected and sampled by gas chromatography (GC) using a mass spectrometer (MS) as a detector. Results of an analysis of the GC-MS trace showed 83.8 area % methanol, 12.2 area % 3-aminopropylmethydimethoxysilane, 0.25 area % bis(methyldimethoxysilylpropyl)amine, 0 area % 2-cyanoethylmethyldimethoxysilane, and 2.3 area % high boiling siloxanes.

This experiment demonstrates that a cobalt supported on kieselguhr catalyst selectively promotes the formation of the primary amine, 3-aminopropylmethyldimethoxysilane, with a 100% conversion based on the starting nitrile. Selectivity of the process for the primary amine, in relation to the secondary amine, was 47 to 1.

EXAMPLE 2

The hydrogenation of 2-cyanoethylmethyldimethoxysilane in the presence of a cobalt supported on alumina catalyst was evaluated. To the reactor was added 30.3 g of 2-cyanoethylmethyldimethoxysilane, 100 g of methanol as solvent, and 4.5 g of cobalt supported on alumina. The cobalt on alumina catalyst was purchased from United Catalyst, Inc. (Louisville, Ky. Cat. No. G-62RS). The catalyst was in the form of a powder containing about 34.5 percent, by weight cobalt. The process was started and conducted under conditions similar to those described for Example 1. After 1.5 hours under reaction conditions, hydrogen consumption had stopped.

The products were then isolated and analyzed as previous described in Example 1. Results of the analysis of the GC-MS trace showed 81 area % methanol, 16.1 area % 3-aminopropylmethyldimethoxysilane, 0.29 area % bis(methyldimethoxysilylpropyl)amine, 0.0 area % 2-cyanoethylmethyldimethoxysilane, and 2.0 area % high boiling siloxanes.

These results demonstrate that a cobalt supported on alumina catalyst selectively promotes the formation of 3-aminopropylmethyldimethoxysilane, with a conversion of 100 % based on the starting nitrile. Selectivity of the process for the primary amine, in relation to the secondary amine, was 54 to 1.

EXAMPLE 3

The hydrogenation of 2-cyanoethyltriethoxysilane in the presence of a cobalt supported on kieselguhr catalyst was evaluated by a process similar to that described in Example 1. To the reactor was added 30.0 g of 2-cyanoethyltriethoxysilane and weights of ethanol and catalyst as described in Table 1. The Cobalt supported on kieselguhr catalyst was as described in Example 1. The temperature at which the process was conducted is presented in Table 1.

After consumption of hydrogen had ceased, the products of the reaction were collected and analyzed by GLC-MS, as previously described. The results are presented in Table 1. The heading "Conversion" denotes the percent of the 2-cyanoethyltriethoxysilane converted to product. The heading "Selectivity" denotes the percent of converted 2-cyanoethyltriethyoxysilane converted to the primary amine. Products are expressed as area % appearing under the GC-MS trace.

TABLE 1

Hydrogenation of 2-Cyanoethyltriethoxysilane in The Presence of a Cobalt on Kieselguhr Catalyst

| | (Run No.) | | | | |
|---|---|---|---|---|---|
| | 29 | 31 | 33 | 35 | 37 |
| Co/kieselguhr (g) | 6 | 6 | 12 | 12 | 18 |
| Temperature (°C.) | 175 | 150 | 150 | 150 | 150 |
| Ethanol (g) | 79 | 79 | 75 | 0 | 79 |
| (EtO)₃SiCH₂CH₂CH₂NH₂ (%) | 8.8 | 29.4 | 29.7 | 4.0 | 16.4 |
| ((EtO)₃SiCH₂CH₂CH₂)₂NH (%) | 0 | 0 | 0 | 0 | 0 |
| (EtO)₃SiCH₂CH2CN (%) | 3.4 | 9.2 | 3.4 | 82 | 17.4 |
| Selectivity (%) | 100 | 100 | 100 | 100 | 100 |
| Conversion (%) | 68 | 76 | 89 | 5 | 48 |

The results demonstrate the selectivity of a cobalt on kieselguhr catalyst in hydrogenating 2-cyanoethyltriethoxysilane to the primary amine containing silane under a variety of catalyst concentrations, reaction temperatures, and with and without solvent.

What is claimed is:

1. A process for hydrogenation of cyanoorganosilanes, the process comprising:
   (a) contacting a cyanoorganosilane of formula

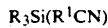
   R₃Si(R¹CN)

with hydrogen gas, in the presence of a catalyst comprising cobalt retained on a solid support, at a temperature within a range of about 50° C. to 250° C. and a pressure within a range of about 200 psig to 2,000 psig: and
   (b) recovering a primary aminoorganosilane of formula

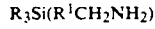
   R₃Si(R¹CH₂NH₂)

where each R is independently selected from a group consisting of alkyl and alkoxy radicals of 1 to 10 carbon atoms, aryl and aryloxy radicals of 5 to 10 carbon atoms, and hydrogen: and $R^1$ is a divalent hydrocarbon radical of 1 to 20 carbon atoms.

2. A process according to claim 1, where R is selected from a group consisting of methyl, methoxy, ethyl and ethoxy.

3. A process according to claim 1, where $R^1$ is ethylene.

4. A process according to claim 1, where the cyanoorganosilane is selected from a group consisting of 2-cyanoethylmethyldimethoxysilane and 2-cyanoethyltriethoxysilane.

5. A process according to claim 1, where contacting the cyanoorganosilane and the hydrogen gas in the presence of a catalyst is effected for a time within a range of 0.5 to 3.0 hours.

6. A process according to claim 1, where the pressure is within a range of about 500 psig to 1,000 psig.

7. A process according to claim 1, where the solid support is selected from a group consisting of silica, alumina, and silica-alumina.

8. A process according to claim 1, where the solid support is kieselguhr.

9. A process according to claim 1, where the cobalt comprises about 10 to 70 weight percent of the total weight of the cobalt and solid support composition.

10. A process according to claim 1, where the process is run as a batch process and the cobalt comprises about 0.1 to 20 weight percent of a mixture comprising the cobalt and the cyanoorganosilane.

11. A process according to claim 1, where the temperature is within a range of about 100° C. to 200° C.

12. A process according to claim 1, where the process is run in the presence of a polar organic solvent.

13. A process according to claim 12, where the polar organic solvent is methanol.

14. A process according to claim 1, where the recovered primary aminoorganosilane is 3-aminopropylmethyldimethoxysilane.

15. A process according to claim 1, where the recovered primary aminoorganosilane is 3-aminopropyltriethoxysilane.

16. A process for hydrogenation of an cyanoorganosilane the process comprising:
    contacting 2-cyanoethylmethyldimethoxysilane with hydrogen gas, in the presence of a catalyst comprising cobalt retained on a solid support selected from a group consisting of kieselguhr and alumina, at a temperature within a range of about 150° C. to 175° C. and a pressure within a range of about 500 psig to 1,000 psig; and recovering 3-aminopropylmethyldimethoxysilane.

17. A process according to claim 16, where the process is run in the presence of methanol.

18. A process for hydrogenation of an cyanoorganosilane, the process comprising:
    contacting 2-cyanoethyltrimethoxysilane with hydrogen gas, in the presence of a catalyst comprising cobalt retained on a solid support selected from a group consisting of kieselguhr and alumina, at a temperature within a range of about 150° C. to 175° C. and a pressure within a range of about 500 psig to 1,000 psig; and recovering 3-aminopropyltrimethoxysilane.

19. A process according to claim 18, where the process is run in the presence of methanol.

* * * * *